United States Patent [19]

Milberger et al.

[11] 4,174,625
[45] Nov. 20, 1979

[54] TRANSDUCER FOR DETERMINING STRAIN DATA DURING PILING

[76] Inventors: Lionel J. Milberger, 19402 Enchanted Oaks Dr., Spring, Tex. 77373; Byrd M. Sasser, Jr., 8B, Southside, College Station, Tex. 77840

[21] Appl. No.: 882,572

[22] Filed: Mar. 2, 1978

[51] Int. Cl.² .............................................. G01N 3/32
[52] U.S. Cl. ........................................................ 73/11
[58] Field of Search ...................... 73/11, 84, 141 A, 12

[56] References Cited

U.S. PATENT DOCUMENTS

| | | | |
|---|---|---|---|
| 3,277,704 | 10/1966 | Eckard | 73/141 A |
| 3,771,359 | 11/1973 | Shoberg | 73/141 A |
| 3,817,091 | 6/1974 | Fredrick | 73/84 |

*Primary Examiner*—Jerry W. Myracle

*Attorney, Agent, or Firm*—Jennings B. Thompson; Marvin B. Eickenroht

[57] ABSTRACT

A transducer is disclosed for placing on top of a pile to indicate the force imposed on the pile by the hammer driving the pile. The transducer includes a body made of a material of a known modulus of elasticity. The body has first and second parallel surface areas on opposite sides thereof that face the pile and the hammer respectively. One of the surface areas comprises the co-planer surfaces of a plurality of spaced flexure elements that are spaced outwardly from the adjacent surface of the body. Each flexure element is connected to the body by supporting arms that are integrally connected to the flexure elements and the body to transmit the force imposed on the flexure elements to the body. Strain gauges mounted on the supporting arms measure the strain in the arms due to the force of the hammer from which the force imposed by the hammer on the pile can be determined.

5 Claims, 5 Drawing Figures

TRANSDUCER FOR DETERMINING STRAIN DATA DURING PILING

This invention relates to a transducer for use in measuring the force imposed upon a pile by a pile-driving hammer.

Stresses that are developed in a pile while the pile is being driven are determined by using the wave equation method of pile driving analysis. One of the factors used in the wave equation method of pile driving analysis is the force imposed on the pile by the hammer. It is extremely difficult to make accurate force measurements on full scale field piles, particularly dynamic force measurements during driving. These measurements in the past have been made by attaching strain gauges to the surface of the pile and connecting them to amplifiers and recorders so that a permanent record of the strain measurement can be made during a typical hammer blow. In the case of metal piles, such as metal-shell pipe piles or "H" beam piles, conventional metal foil strain gauges or "weldable" strain gauges are attached to prepared areas on the metal surface.

In the case of prestressed concrete piles, one practice used in the past is a cast-in-place strain gauges. These gauges must be attached to the reinforcing steel, properly oriented and wired into an appropriate electrical bridge circuit arrangement prior to the time that the concrete for the pile is cast into the form. This requires access to the pile forms at a time prior to casting the concrete. This instrumenting procedure is difficult and expensive. Further, the strain gauge instrumentation is required to survive the casting process and to further remain functional during pile curing, removal from the forms, storage, and transport to the job site where it is to be driven. Experience has proven that the survival rate is not very good.

Another difficulty with this force measuring technique for prestressed concrete piles is calibration. To compute forces from the strain measurements, the elastic modulus must be known for the particular concrete that is being used. Further, Poisson's ratio is also needed depending on the manner in which the pile is instrumented. Both these elastic properties are difficult to determine and varies considerably with each concrete mix. Additionally, other variables must be known such as pile cross-sectional area, gauge factor of the gauges, and lead wire effects in connection with the shunt calibration technique being used. All these varibles contribute to errors.

It is an object of this invention to provide an improved transducer for use in measuring the force imposed on a pile by the hammer driving the pile that will reduce or eliminate the problems described above and reduce the cost of making such measurements.

It is a further object of this invention to provide a transducer for use in measuring the force imposed on a pile while piling that is positioned between the hammer and the pile and transmits the force of the hammer directly to the pile.

Another problem with strain gauges mounted as described above is their limited ability to sense offset or eccentric forces on the pile caused when the hammer does not hit the pile squarely, and it is another object of this invention to provide a transducer of the type described that includes sensing elements that are distributed over the active area under the hammer to accurately measure inclined or eccentric blows on the pile by the hammer.

These and other objects, advantages and features of this invention will be apparent to those skilled in the art from a consideration of this specification including the attached drawings and appended claims.

Figure 1:
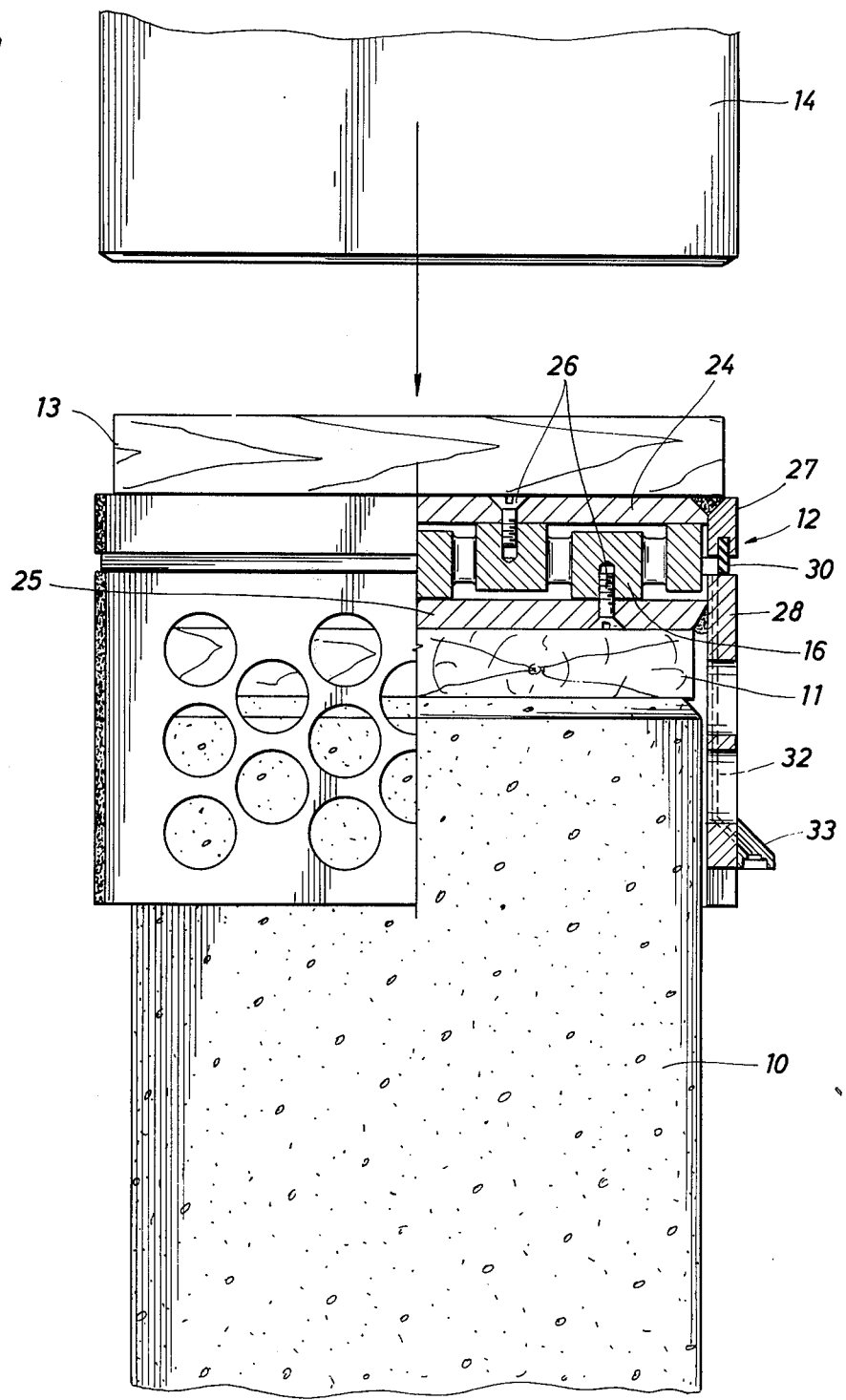
FIG. 1 is a view partly in section and partly in elevation of the preferred embodiment of the transducer of this invention in position on top of a pile between the pile and the hammer.
Figure 2:
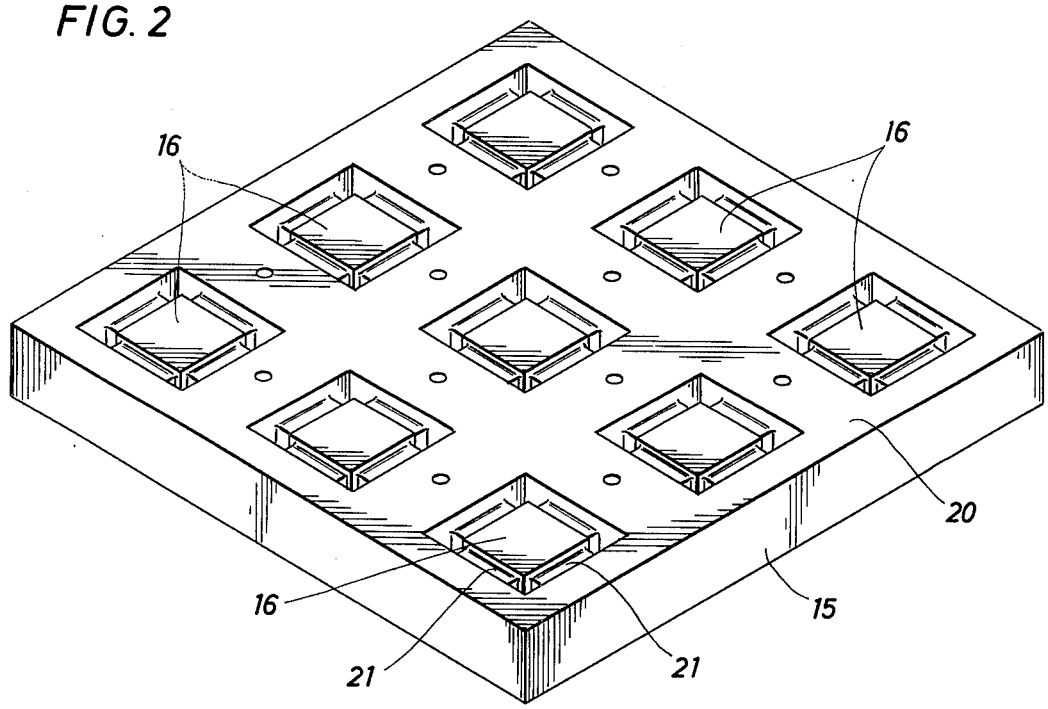
FIG. 2 is an isometric view of the top of the body of the transducer.

The embodiment of the transducer of this invention that is shown in the drawings is one designed for use with piles that are square in cross section such as the typical reinforced pre-stressed concrete piles. Such a pile is indicated by the number 10 in FIG. 1 where only the top of the pile is shown. Cushion 11 is positioned on top of pile 10 between the top of the pile and transducer 12. On top of the transducer is cap block 13 which receives the direct impact of hammer 14 as the pile is being driven into the ground.

Cushion 11 and cap block 13 are usually made of wood. Cushion 11, for example, may consist of three layers of 2" green oak usually positioned with the grain horizontal. Cap block 13 is commonly made up of three or four layers of plywood, each layer being usually about ¾" thick.

Transducer 12 includes body 15 made of a material having a known modulus of elasticity, such as aluminum or steel. Aluminum is preferred since it is lighter. In accordance with this invention, the body of the transducer has a first portion with a surface area facing the pile for transmitting the force of the hammer to the pile and a second portion with a surface area facing the hammer to receive the force of the hammer. In other words, the body has first and second parallel surface areas on opposite sides thereof for facing the pile and the hammer respectively. The portions of the body providing the two surface areas are connected by support arms that transmit the force of the hammer from one portion of the body to the other and means are attached to the arms for providing a signal proportional to the strain produced in the arms by the force of the hammer on the transducer.

Figure 3:
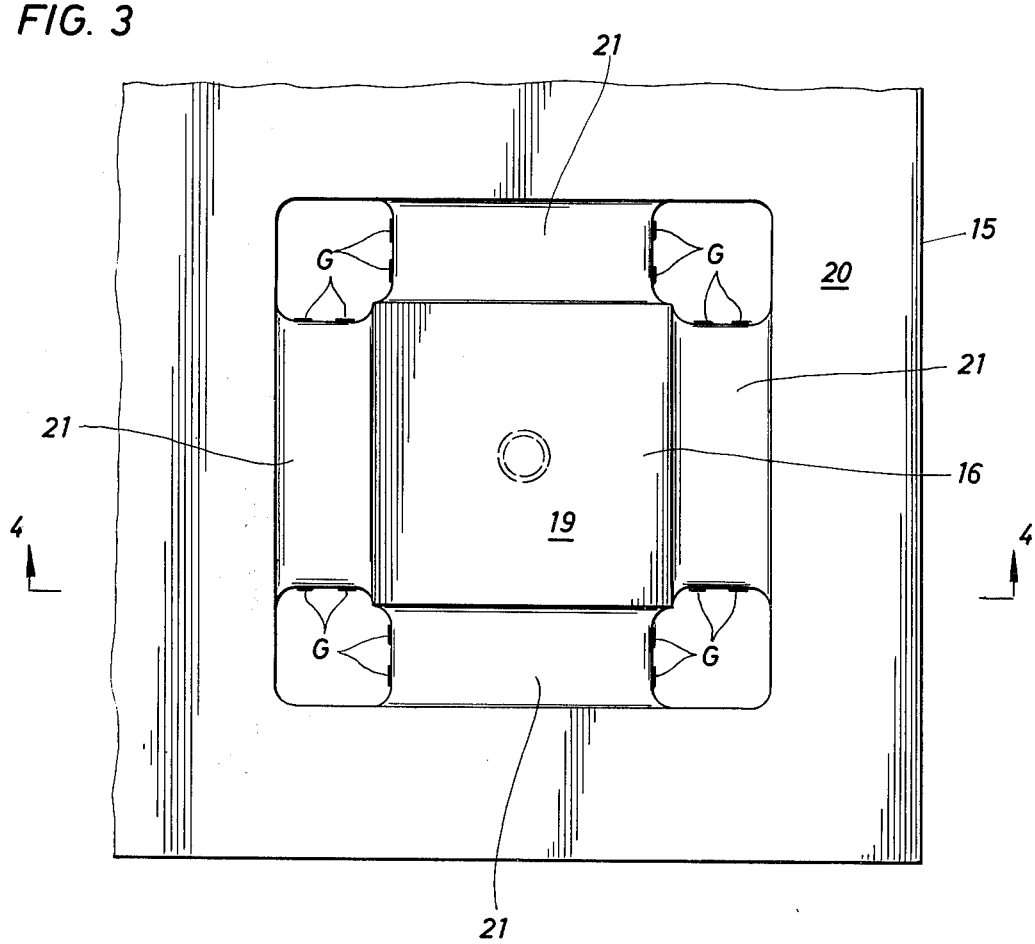
FIG. 3 is a top view of an enlarged scale one of the flexure or sensing elements of the transducer.
Figure 4:
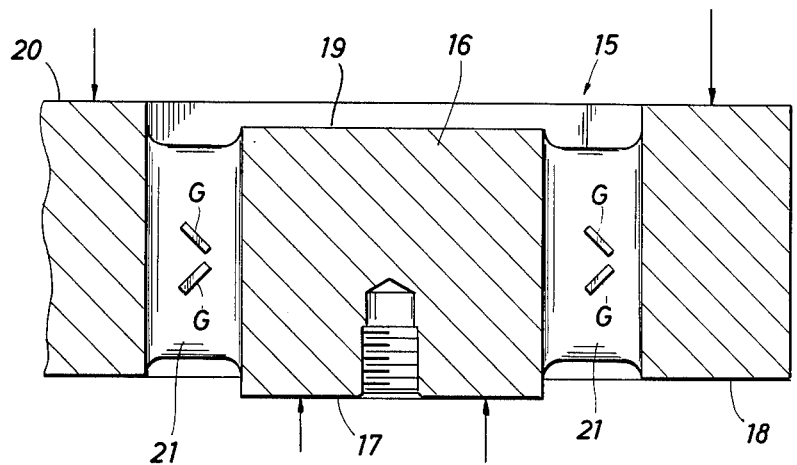
FIG. 4 is a view taken along line 4—4 of FIG. 3.

In the embodiment shown, the portion of the body providing one surface area for receiving either the force of the hammer or for transmitting the force to the pile comprises a plurality of flexure elements 16. As best seen in FIGS. 3 and 4, where one flexure element is shown on an enlarged scale, the flexure element comprises a portion of the body that is generally rectangular in cross section having surface 17 that extends outwardly beyond surface 18 of the body. On the opposite side of the flexure element, side 19 is positioned below the plane of surface 20 of the body. Flexure element 16 is supported and integrally connected to body 20 by four support arms 21. Thus a downward force, as shown in FIG. 4, imposed on surface 20 of the body of the transducer by the hammer produces a reactive force on surface 17 of the flexure element by the resistance of the pile. Support arms 21 will be stressed as beams and strain will be produced that is proportional to the force imposed on the transducer by the hammer. Strain gauges, indicated by the letter G, are positioned as shown in FIGS. 3 and 4 to measure the strain created or produced in the support arms by the force of the hammer. The strain gauges should be positioned so that one is placed in compression and one is placed in tension. Generally this can be accomplished by locating the gauges as shown extending at a 45° angle to the neutral axis of the beam and positioned on opposite sides of the neutral axis and at an angle of 90° to each other.

Figure 5:
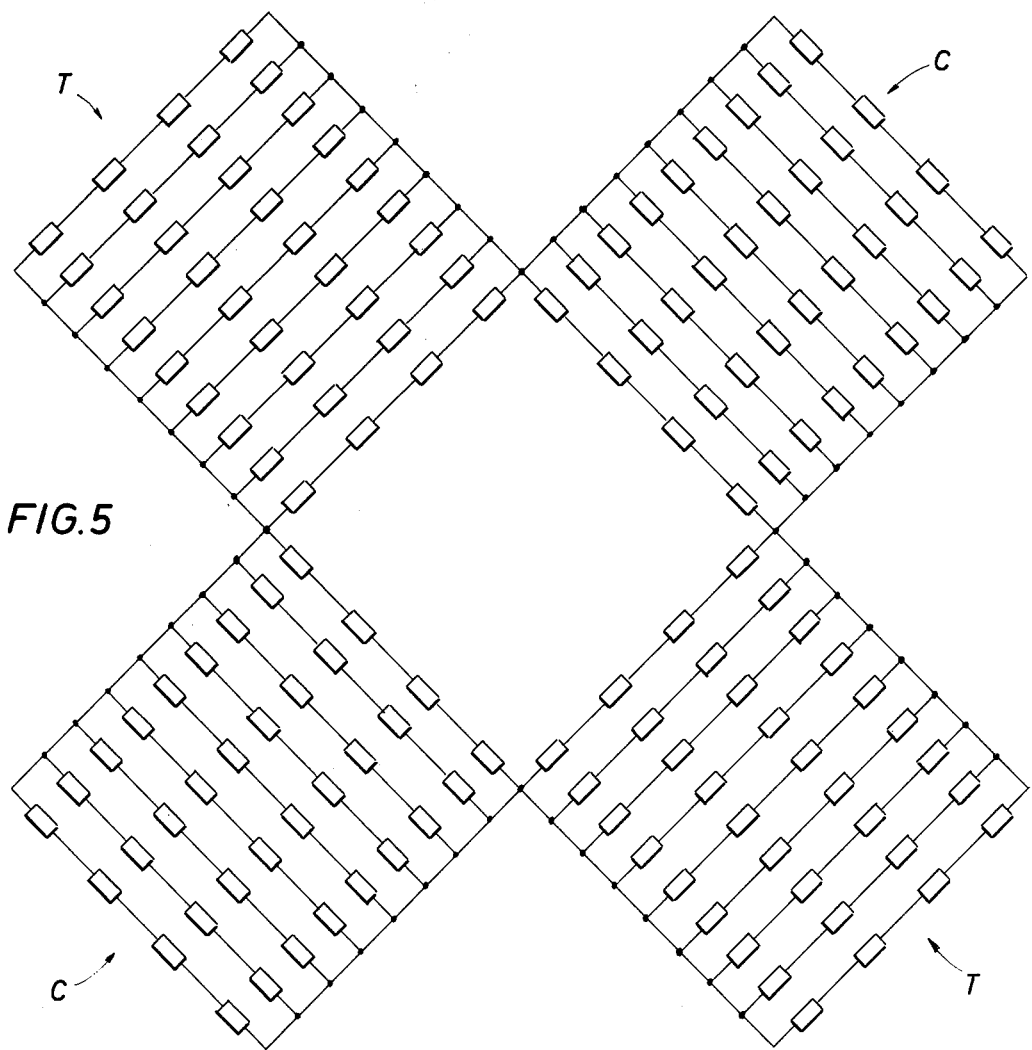
FIG. 5 is an electric circuit diagram illustrating the manner in which the strain gauges employed with the transducer are connected to provide the desired signal for determining the force imposed on the pile by the hammer.

The conventional manner of arranging the strain gauges in the circuit is shown in FIG. 5. The gauges are connected as a wheatstone bridge. The gauges in compression, indicated by the letter "C" are divided equally in opposite legs while the gauges in tension, indicated by the letter "T" are divided equally in the opposite legs of the bridge.

The strain gauges are part of a circuit designed to process the signals from the strain gauges and indicate the force imposed on the pile by the hammer. One such system is described in U.S. Pat. No. 4,052,884 entitled Method and Apparatus for Determining Strain Data During Piling, which issued on Oct. 11, 1977. Also, a dynamic pile force readout system that can be used with the transducer of this invention is described in research report No. 174-1F of the Texas Transportation Institute, Texas A & M University, College Station, Tex., published in August, 1974 and entitled "Operating Instructions for Dynamic Pile Force Readout, Model 2174," by Milberger, L.J. and Zimmer, R.A.

To help protect the body of the transducer and the strain gauges attached thereto from the elements when in use in the field, the body is enclosed, in the manner shown in FIG. 1. Upper plate 24 and lower plate 25 are attached to the body by cap screws 26 as shown. Upper plate 24 has downwardly extending skirt 27 that encircles a portion of the body and lower plate 25 has skirt 28 a portion of which extends above the plate and encircles the body but is spaced from the lower edge of skirt 27. Resilient seal member 30 is positioned between the skirts, as shown in FIG. 1, to provide a seal that allows the two skirts to move together under the force of the hammer, but which keeps moisture, dirt and the like from entering the enclosed area where the body of the transducer is located.

Skirt 28 also extends downwardly to encircle the top of the pile to keep the transducer assembly in position during the driving of the pile. Also, skirt 28 is provided with groove 32 through which the lead lines from the transducer can be brought to connector plug 33 for connection to signal processing apparatus such as the type described in the patent identified above or the paper.

Holes may be provided in skirt 28, if desired, to reduce the overall weight of the transducer assembly.

From the foregoing, it will be seen that this invention is one well adapted to attain all of the ends and objects hereinabove set forth, together with other advantages which are obvious and which are inherent to the apparatus and structure.

It will be understood that certain features and subcombinations are of utility and may be employed without reference to other features and subcombinations. This is contemplated by and is within the scope of the claims.

As many possible embodiments may be made of this invention without departing from the scope thereof, it is to be understood that all matter herein set forth or shown in the accompanying drawings is to be interpreted as illustrative and not in a limiting sense.

The invention having been described is:

1. A transducer for placing between a pile and a pile driving hammer to provide a signal proportional to the force imposed on the pile by the hammer comprising a body of material of a known modulus of elasticity, said body having a first portion with a surface area facing the pile for transmitting the force of the hammer to the pile and a second portion with a surface area facing the hammer to receive the force of the hammer one of said portions including a plurality of symmetrically spaced flexure elements having surfaces of equal force receiving area and supporting arms of equal length and cross section connecting each flexure element to the other portion for transmitting the force of the hammer from the flexure elements to the other portion, and means attached to the arms for providing a signal proportional to the strain produced in the arms by the force of the hammer on the second surface.

2. The transducer of claim 1 in which the signal producing means includes electrical elements having a resistivity that varies in proportion to the strain in the arms to which they are attached.

3. A transducer for placing on the top of a pile to transmit the force of a pile driving hammer from the hammer to the pile and to provide strain data for use in determining the force imposed on the pile by the hammer, comprising a body of metallic material of a known modulus of elasticity having first and second parallel surface areas on opposite sides thereof for facing the pile and the hammer respectively, one of said surface areas comprising the co-planer surfaces of a plurality of symmetrically spaced flexure elements, said co-planer surfaces of the flexure elements being spaced outwardly from the adjacent surface of the body, four support arms attaching each flexure element to the body to transmit the force imposed on the flexure element to the body, said arms being arranged with the arms on opposite sides of the flexure element having a common longitudinal axis that is perpendicular to the longitudinal axis of the other two arms, and means for measuring the strain in the arms due to the force of the hammer.

4. The transducer of claim 3 further provided with an upper flat-sided plate and a lower flat-sided plate attached to the body on opposite sides, each plate having a skirt attached thereto that encircles a portion of the body, and a resilient seal member encircling the body and positioned between the skirts to combine with the skirts to enclose the body while allowing relative movement of the skirts as required by the strain of the body.

5. A strain gauge transducer for use in determining strain data during piling comprising a generally flat-sided metal body for positioning between the top of a pile and a pile driving hammer, said plate having a plurality of symmetrically spaced flexure elements formed therein that extend above the adjacent surface of the body on one side and are recessed relative to the adjacent surface of the body on the other side, a plurality of arms integrally attached to the flexure elements and the body, and extending between the flexure elements and the body with adjacent arms having mutually perpendicular longitudinal axes, and strain gauges positioned on the arms to measure the strain in the arms due to the force imposed on the flexure members by a hammer.

* * * * *